United States Patent [19]

Bergeron et al.

[11] Patent Number: 5,968,480
[45] Date of Patent: Oct. 19, 1999

[54] ORAL COMPOSITION EXHIBITING ENHANCED ANTIPLAQUE EFFICACY

[75] Inventors: Vance Bergeron; Jean-Pierre Marchand, both of Lyon; Harold Schoonbrood, Paris, all of France; Yelloji Rao K. Mirajkar, Picataway, N.J.

[73] Assignee: Colgate Palmolive Company, New York, N.Y.

[21] Appl. No.: 09/112,542

[22] Filed: Jul. 9, 1998

[51] Int. Cl.⁶ .................................................. A61K 7/16
[52] U.S. Cl. ............................................................ 424/49
[58] Field of Search ........................................ 427/47–58

[56] References Cited

U.S. PATENT DOCUMENTS

| | | | |
|---|---|---|---|
| 5,252,318 | 10/1993 | Joshi et al. | 424/78.04 |
| 5,256,401 | 10/1993 | Duckenfield et al. | 424/49 |
| 5,603,955 | 2/1997 | Gehrke et al. | 424/484 |
| 5,605,676 | 2/1997 | Gaffar et al. | 424/47 |
| 5,674,521 | 10/1997 | Gehrke et al. | 424/423 |
| 5,690,911 | 11/1997 | Mirajkar et al. | 424/49 |
| 5,726,456 | 3/1998 | Lupton et al. | 252/182.21 |
| 5,800,803 | 9/1998 | Mirajkar et al. | 424/55 |
| 5,840,338 | 11/1998 | Roos et al. | 424/488 |
| 5,843,406 | 12/1998 | Mordarski et al. | 424/49 |

FOREIGN PATENT DOCUMENTS

| | | |
|---|---|---|
| 342073 | 11/1989 | European Pat. Off. . |
| 539256 | 4/1993 | European Pat. Off. . |
| 95/24430 | 9/1995 | WIPO . |
| 97/00275 | 1/1997 | WIPO . |

OTHER PUBLICATIONS

Adachi et al., Polymer J. 14(12):985–992 Complex–Forming Polyoxyethylene: Pol(Acrylic acid) Systems[1], 1982.

DE Vos et al Polymer 35:2644–2650 Synthesis and characterization of poly(acrylamide)–graft–poly(ethylene oxide––co–propylene oxide), 1994.

Hourdet et al 35:2624–2630 Reversible thermothickening of aqueous polymer solutions (PEO–modified Poly(aerylic acid) (PAA/PEO), 1994.

*Primary Examiner*—Shep K. Rose
*Attorney, Agent, or Firm*—Paul Shapiro

[57] ABSTRACT

A composition and method for the treatment and prevention of plaque accumulation on teeth wherein there is administered to the oral cavity an oral composition comprising an orally acceptable aqueous vehicle containing an effective therapeutic amount of a noncationic antibacterial agent and an acrylic polymer/polyoxyalkylene copolymer formed from about 80 to about 90% by weight of the acrylic polymer and about 5 to about 20% by weight of the polyoxyalkylene having a molecular weight greater than 4,000 and less than 20,000 the antibacterial compound exhibiting increased antiplaque activity on dental tissue.

18 Claims, No Drawings

ORAL COMPOSITION EXHIBITING ENHANCED ANTIPLAQUE EFFICACY

BACKGROUND OF THE INVENTION

1. Field of the Invention

The present invention relates to oral care compositions exhibiting improved antiplaque activity on dental tissue of noncationic antibacterial compounds.

2. The Prior Art

Intraoral surfaces, either soft or hard, frequently are covered by a bacterial deposit called "plaque". Such dental plaque is a soft deposit which adheres tenaciously at the points of irregularity or discontinuity on dental tissue, e.g., on rough calculus surfaces, at the gum line and the like. Plaque generally consists of about 70% by weight bacteria, with the balance comprised of host cells, food debris, proteins, polysaccharides, etc. Besides being unsightly, plaque is implicated in as a causative factor in caries and periodontitis, which together are responsible for about 95% of tooth loss.

As disclosed in U.S. Pat. No. 5,043,154 a wide variety of noncationic antibacterial agents have been suggested in the art to retard plaque formation and the oral infections and dental disease associated therewith. For example, halogenated hydroxydiphenyl ether compounds such as Triclosan are well known to the art for their antibacterial activity and have been used in oral compositions to counter plaque formation.

Although antibacterial agents such as Triclosan are highly effective, it is difficult to deliver an effective therapeutic level of such agents on dental tissue. As disclosed in U.S. Pat. No. 4,894,220, and U.S. Pat. No. 5,032,386 certain polymeric polycarboxylates, such as vinyl ether-maleic anhydride copolymers, enhance the delivery of the antiplaque agent on dental tissue, and consequently enhance the antiplaque efficacy of these agents.

Accordingly, the greater the amount of antibacterial compound delivered to infected areas of dental tissue by saliva present in the mouth the more efficacious the antiplaque effect. There is therefore a continuous interest in the art to provide means whereby nonionic antibacterial compounds contained in oral care compositions can be more efficaciously delivered to dental tissue.

SUMMARY OF THE INVENTION

In accordance with this invention there is provided an oral composition comprising in an orally acceptable aqueous vehicle, an effective antiplaque amount of a noncationic antibacterial agent and an amount of a carboxylated copolymer formed from an acrylic polymer and a polyoxyalkylene selected from (a) an acrylic polymer/polyoxyalkylene block copolymer wherein the polyoxyethylene has a molecular weight greater than about 4000 and less than 20,000 grams/mole (g/mol) and (2) a graft copolymer of a polymerized acrylic monomer on a polyoxyalkylene backbone wherein the polyoxyalkylene has a weight average molecular weight greater than about 5000 and less than about 50,000 g/mol. The presence in the oral composition of the carboxylated block and/or graft copolymer significantly enhances the uptake of the noncationic antibacterial agent to oral surfaces, whereby the antiplaque therapeutic efficacy of the administered composition is significantly enhanced.

DETAILED DESCRIPTION OF THE INVENTION

The term "molecular weight" as used in the specification and claims herein means weight average molecular weight.

The acrylic polymer/polyoxyalkylene copolymers of the present invention contain polymeric segments obtained from the polymerization of an acrylic monomer which is attached to another polymer chain which is comprised of oxyalkylene monomers. The resulting copolymers are soluble in aqueous medium. The copolymer can be either a block copolymer or a graft copolymer.

The term "block copolymer" as used herein means a copolymer which has a long chain segment of one polymerized monomer such as an acrylic monomer followed by a long chain segment of another polymerized monomer such as an oxyalkylene monomer. Block copolymers are prepared by the covalent coupling of one homopolymer to the terminus of a second, different homopolymer. A block copolymer containing homopolymer A and homopolmer B may schematically be represented by the formula

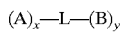

where $(A)_x$ is a homopolymer of x monomers of A, and $(B)_y$ is a homopolymer consisting of y monomers of B, and L is a suitable covalent bond.

The term "graft copolymer" as used herein means a polymer chain such as polyoxyalkylene, referred to in the art as the "backbone" which has pendant chains of another polymer such as an acrylic polymer attached at intervals along the backbone. A graft copolymer having backbone homopolymer A onto which a second pendant homopolymer is attached may be schematically represented by the formula:

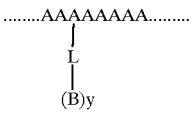

where AAAAAAAA is a homopolymer of monomer A, (B)y is a homopolymer of y monomers of B and L is a suitable covalent bond.

The term "acrylic" as used herein means an alpha, beta-ethylenically unsaturated monomeric compound, preferably a carboxylic acid, an alkyl ($C_1$–$C_8$) ester or hydroxylated alkyl ($C_1$–$C_8$) ester of such carboxylic acid. Compounds encompassed by the term "acrylic monomer" include acrylic acid, methacrylic acid, maleic acid or anhydride and itaconic acid. Ester derivatives of the above mentioned acids such as 2-hydroxy propyl acrylate, methacrylate and 2-ethyl hexyl acrylate are also within the perview of the term acrylic.

The term "acrylic polymer" as used herein means polymers characterized as being derived from acrylic monomers.

The term "polyoxyalkylene" as used herein means polymeric materials having the formula

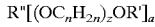

wherein R' is a hydrocarbon radical containing up to 10 carbon atoms which is free of aliphatic unsaturation and has a valence of a, a is an integer having a value of 1 to about 4, R" is a hydrogen atom or a monovalent hydrocarbon radical containing up to 6 carbon atoms which is free of aliphatic unsaturation, n has a value of 2 to 4 inclusive, and z is an integer representing repeating monomer units.

In general, polyalkylene compounds contain either oxyethylene groups or oxyethylene groups and higher oxyalkylene groups such as oxypropylene and oxybutylene groups, either in random or block distribution in their molecules. The polyoxyalkylenes may be made by processes well known in the art by reacting an alkylene oxide or mixtures of alkylene oxides with a compound having from one up to as many as four active hydrogen atoms, such as water, monohydroxylic alcohols such as ethanol and propanol, dihydroxylic alcohols such as ethylene glycol and the monoethyl ether of glycerine. The polyoxyalkylene products of such reactions will have linear or branched oxyalkylene or oxyethylene-higher oxalkylene chains, and such chains will terminate with hydroxyl groups which are reactive with acrylic monomers or polymers to form graft or block copolymers used in the practice of the present invention.

Examples of polyoxyalkylene compounds suitable for use in the practice of the present invention include polyoxyethylene (POE), polyoxyethylene-polyoxypropylene (POE-POP) diblocks and POE-POP-POE triblocks.

The carboxylated copolymers used in the practice of the present invention can be obtained according to known techniques for the preparation of block or graft copolymers.

Thus, the block copolymers can be obtained by covalent coupling of the polyoxyalkylene and the acrylic polymer using groups such as amide, ester, ether, thioester, thioether, urea, urethane, amine or others resulting from the reaction of the terminal functions of the two types of polymer as described in WO 95/24430. They can also be obtained by radical polymerization of one or more acrylic monomers, in the presence of the polyoxyalkylene and functionalized with xanthate or thiuram unit, as described in EP-A-539,256, EP-A-342,073 and EP-A-418,116. WO 95/24430, Hoffman et al (University of Washington) on pages 48 to 58 describes and claims antimicrobial drug releasing coplymer gels of topical and block or graft coplymers of acrylic acid and polyoxyalkylene monomer.

Graft copolymers which comprise an polyalkylene backbone and one or more acrylic polymer grafts can be obtained by radical polymerization or irradiation, in aqueous phase or in bulk, of the acrylic monomer in the presence of a polyalkylene. This technique is described, for example, in WO 97/00275. WO 97/00275, Bromberg et al (Gel Services, Inc.) on pages 39 and 67 to 78 describe and claim the synthesis of oral or topical during delivery response polymer networks of acrylic acid and polyalkylene monomers.

The radical polymerization to prepare the copolymer is preferably performed by polymerizing the acrylic monomer (s) in the aqueous phase containing the polyoxyalkylene, in the presence of a polymerization initiator which is preferably water soluble, at a temperature of about 20 to 100° C., preferably of about 50 to 95° C. Examples of polymerization initiators include water soluble initiators such as alkaline persulfates, redox systems based on an oxidizing agent such as aqueous hydrogen peroxide solution or alkaline persulfates, and on a reducing agent such as alkaline bisulfites, or azo initiators such as azobisisobutyro-nitrile, 2,2'-azobis[2-methyl-N-(2-hydroxyethyl)-proionamide] or 4.4'-azobis(4-cyanovaleric acid). The amount of initiator used can be from about 0.01 to 2%, preferably from 0.05 to 0.3%, by weight relative to the total weight of ethylenically unsaturated monomers and polyoxyalkylene compound.

In the preparation of the graft copolymer, preferably the acrylic monomer is introduced continuously into an aqueous reaction medium containing the polyoxyalkylene and the initiator, at a temperature of about 20 to 100° C., preferably about 50 to 95° C. The graft copolymer obtained comprises as the backbone, a polyoxyalkylene having the acrylic polymer grafted on the polyoxyalkylene backbone in the form of side chains at individual carbon atoms of the polyoxyalkylene chain in the form of an aqueous solution containing about 10 to 30% solids. If desired, it can be separated from the aqueous medium, for example by drying or acidification.

The block and graft copolymers used in the preparation of the oral compositions of the present invention have molecular weights in the range of from 250,000 to 1,000,000 g/mol and preferably in the range of 500,000 to 1,000,000 g/mol. The polyoxyethylene component constitutes about 5 to about 25% by weight and preferably about 10 to about 20% by weight of the copolymer and the acrylic polymer component constitutes about 75 to about 95% by weight of the copolymer and preferably about 80 to about 90% by weight.

The polyoxyalkylene component of the block copolymer has a molecular weight of greater than about 4000 and less than 2000 g/mol. As will hereinafter be demonstrated, it is critical to the practice of the present invention that the molecular weight of the polyoxyalkylene component of the block copolymer be greater than about 4000 and less than 20,000 g/mol as block copolymers containing a polyoxyalkylene component outside this molecular weight range provide limited enhancement of noncationic antibacterial agent therapeutic activity when delivered to oral tissue from oral compositions.

The polyoxyethylene component of the acrylic polymer/ polyoxyethylene graft copolymer used in the practice of the present invention has a molecular weight of 10,000 to 50,000 g/mol and preferably about 20,000 to 40,000g/mol.

The acrylic polymer/polyoxyalkylene block or graft copolymer is incorporated in the oral composition of the present invention at a concentration of about 0.5 to about 5% by weight and preferably about 1 to about 3% by weight.

The term "oral composition" as used herein designates dental products which, in the ordinary course of usage, are retained in the oral cavity for a time sufficient to contact substantially all of the dental surfaces, but are not intentionally ingested. Such products include, but are not limited to, dentifrices, gels, mouthwashes, chewing gums and lozenges.

In the preparation of an oral composition, in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 30% to about 60% by weight and the humectant concentration typically totals about 40 to about 60% by weight of the oral composition.

In the practice of the present invention, the noncationic antibacterial agent is present in the oral composition in an effective antiplaque amount, typically about 0.01 to about 2% by weight, preferably about 0.1 to about 1% by weight. Noncationic antibacterial agents useful in the practice of the present invention are phenolic compounds of the type disclosed in U.S. Pat. No. 5,368,844, which disclosure is herein incorporated by reference. Typical phenolic compounds include phenol and its homologs, such as 2,4-dimethylphenol, 4-n-butyl phenol, 4-n-amyl phenol and 4-n-heptyl phenol, 2-methoxy-4-(2 propenyl)-phenol and 2-isopropyl-5-methyl phenol; mono and polyalky and aromatic halophenols, such as 4-chloro-2-methyl phenol, 5-chloro-2-hydroxydiphenylmethane, 2-phenyl phenol, n-hexyl 0-bromophenol, and 6-iso-propyl-2-ethyl-3-methyl p-chlorophenol; resorcinol. Halogenated hydroxy di-phenyl ethers such as Triclosan are preferred.

In the preparation of the oral compositions of the present invention anionic surfactants are included in the composition for production of foam and to aid in cleaning and removal of debris; these anionic surfactants include the higher fatty acid monoglyceride monosulfates, such as the sodium salts of the monosulfated monoglycerides of hydrogenated coconut oil fatty acid; alkyl sulfates, such as sodium lauryl sulfate; alkyl aryl sulfonates, such as sodium linear dodecyl benzene sulfonate, olefin sulfonates, such as sodium olefin sulfonate in which the olefin group is 12 to 21 carbon atoms; alkyl alkali sulfoacetates such as sodium lauryl sulfoacetate; higher fatty acid esters of 1,2-dihydroxypropane sulfonates; the substantially saturated higher aliphatic acyl amides of lower aliphatic aminocarboxylic acid alkali metal salts, such as those having 12 to 16 carbon atoms in the fatty acyl radicals; higher alkyl poly-lower alkoxy sodium sulfates, higher fatty acid sodium ad potassium soaps of coconut oil and tallow, and the like. The anionic surfactant, sodium lauryl sulfate, is preferred for use in the practice of the present invention.

The anionic surfactant is included in the oral composition of the present invention at a concentration of a bout 0.1 to about 5% by weight and preferably about 0.5 to about 3% by weight.

The oral composition when in the form of a dentifrice, such as toothpaste, also typically contains a polishing material such as crystalline silica, having a particle size of up to about 20 microns, such as commercially available Zeodent 115, silica gel or colloidal silica, complex amorphous alkali metal aluminosilicates, hydrated alumina, calcined alumina, sodium metaphosphate, sodium bicarbonate, calcium carbonate, calcium pyrophosphate, dicalcium phosphate and dicalcium phosphate dihydrate. Typically, the polishing material is included in semi-solid or pasty dentifrice compositions of the present invention in an amount of from about 15 to about 60% by weight and preferably from about 20 to about 55%.

Pyrophosphate salts having antitartar efficacy such as a dialkali or tetraalkali metal phosphate salts such as $Na_4P_2O_7$, $Na_2K_2P_2O_7$, and $K_2H_2P_2O_7$, long chain polyphosphates such as sodium hexametaphosphate and cyclic phosphate such as sodium trimetaphosphate may be incorporated in oral compositions of the present invention preferably at concentration of about 0.5 to about 8.0% by weight and preferably about 0.5 to about 3.0% by weight. In liquid oral preparations, the pyrophosphate salts are incorporated at a concentration of about 0.1 to abut 2% by weight.

Dentifrices prepared in accordance with the present invention typically contain a natural or synthetic thickener in proportions of about 0.1 to abut 5% by weight, preferably about 0.5 to about 2% by weight. Suitable thickeners include irish moss, I-carrageean, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose and colloidal silica.

The oral composition may also contain a source of fluoride ions, or fluoride providing compound, as an anticaries agent, in an amount sufficient to supply about 25 ppm to 5,000 ppm of fluoride ions and preferably 500 to 1500 ppm fluoride ions. Among these compounds are inorganic water soluble fluoride salts, such as the alkali metal salts, for example, sodium fluoride, potassium fluoride, sodium fluorosilicate, ammonium flourosilicate and sodium monofluorophosphate, as well as tin fluorides, such as stannous fluoride and stannous chloride.

Any suitable flavoring or sweetening material may also be employed in the preparation of the oral compositions of the present invention. Examples of suitable flavoring constituents include flavoring oils, e.g., oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together comprise from about 0.1% to 5% more of the oral composition.

Various other materials may be incorporated in the oral preparations of this invention such as whitening agents, including urea peroxide, calcium and hydrogen peroxide, preservatives, vitamins such as vitamin B6, B12, C, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The manufacture of the oral composition of the present invention is accomplished by any of the various standard techniques for producing such compositions. To make a dentifrice, a vehicle is prepared containing a humectant such as glycerol, sorbitol, propylene glycol, gelling agents, an acrylic polymer/polyoxyalkylene copolymer and a noncationic antibacterial agent such as Triclosan. One or more surfactants are added to the vehicle, followed by blending in of a polishing agent, as well as, any polyphosphate and fluoride salts. Finally, any flavoring agent is admixed and the pH of the composition is adjusted to between 6.8 to 7.0.

The following examples are further illustrative of the present invention, but it is understood that the invention is not limited thereto. All amounts and proportions referred to herein and in the appended claims are by weight, unless otherwise so stated.

The molecular mass of the block and graft copolymers used to prepare the dentifrices of the examples were measured by Gel Permeation Chromatography under the following conditions: four (4) columns TSK gel; eluent of water/acetonitrile 80/20 vol. % plus 0.1 M sodium nitrate plus 150 ppm sodium azide; and flowrate 1 ml/mn. The molecular mass is reported as weight average molecular weight.

EXAMPLE 1

The effect of an acrylic polymer/polyoxyalkylene block copolymer of the present invention on noncationic antibacterial agent uptake on dental tissue was assessed using disks of hydroxyapatite (HAP) available from Clarkson Chromatography Products, Inc., which were saliva coated (SCHAP), as an in vitro model for human teeth. This in vitro model has been found to be predictive of in vivo uptake of antibacterial agents on dental tissue.

The uptake of Triclosan on SCHAP disks from a dentifrice composition having the ingredients listed in Table I below containing Triclosan, and an acrylic polymer/polyoxyalkylene block copolymer, namely a polyacrylic acid-polyoxyethylene (PAA-POE) block copolymer having a weight average molecular weight of 1,000,000 containing 12% by weight polyoxyethylene (POE) having a weight average molecular weight of 10,000 designated "Composition A" was determined using SCHAP disks treated with the dentifrice slurry compositions identified in Table I. The amounts of dentifrice slurry used to contact the disks simulated in vivo surface to volume ratios found in the mouth. The dentifrice slurries were a liquid phase solution which contained all the components of a dentifrice except the abrasive. The liquid phase, in part, simulates brushing condition. After incubation for 30 minutes at 37° C., the SCHAP disks were removed from the dentifrice slurry and washed three times with water. The uptake absorption of Triclosan, on SCHAP disks, from Composition A is set forth in Table II, below.

For purposes of comparison, the procedure of Example I was repeated, except comparative polyacrylic acid/polyoxyethylene block copolymers of varying weight average molecular weight containing 12% by weight POE of varying weight average molecular weight were substituted at the 2% weight level for the PAA/POE block copolymer used to prepare Composition A. These comparative PAAIPOE block copolymers include:

PAA/POE block copolymer having a weight average molecular weight 1,000,000 containing 12% by POE having a weight average molecular weight of 20,000 designated "Composition $C_1$".

PAA/POE block copolymer having a weight average molecular weight of 354,000 containing 12% POE having a average weight molecular weight of 4,000, designated "Composition $C_2$".

PAA/POE block copolymer, having weight average molecular weight of 59,600 containing 12% POE having a weight average molecular weight of 4,000, designated "Composition $C_3$".

For purposes of control, 2% by weight Gantrez S-97 a maleic anhydride/vinyl ether copolymer having a weight average molecular weight of 750,000 was substituted for the PAAIPOE block copolymer used in the preparation of Composition A, designated "Composition $C_4$".

The uptake of Triclosan from dentifrice Compositions A, $C_1$–$C_4$ is summarized in Table II below.

TABLE I

| Ingredients | Composition Wt. % |
|---|---|
| Sorbitol | 20.00 |
| Glycerol | 20.00 |
| Propylene Glycol | 0.50 |
| Sodium Lauryl Sulphate | 1.50 |
| PAA/POE Block Copolymer* | 11.56 |
| Triclosan | 0.30 |
| NaF | 0.243 |
| Water | 53.857 |
| Flavor Oil | 1.00 |
| NaOH | 0.60 |
| Total | 100.000 |

*Added as 17.3% solids solution, Wt. % as solids, 2%.

TABLE II

| Composition | Triclosan Uptake (μg/disk) | Standard Deviation* |
|---|---|---|
| A | 107.63 | ±4.24 |
| $C_1$ | 92.73 | ±5.40 |
| $C_2$ | 75.77 | ±2.64 |
| $C_3$ | 56.49 | ±2.53 |
| $C_4$ | 81.42 | ±7.41 |

*Standard Deviation ± from μg of Uptake shown.

The results presented in Table II show that uptake of Triclosan on SCHAP disks was appreciably higher for Compositions A and $C_1$ when compared to the control $C_4$.

EXAMPLE II

The antiplaque efficacy of Compositions A and $C_1$ was compared in vitro to a standard dentifrice containing 2% by weight of Gantrez S-97 (designated "Composition $C_5$") using the Chemostat Plaque Model as described in Gaffar et al, Am. J. Dent. Vol. 3, Special Issue pages S8-S9 (September 1990). The experimental apparatus includes a Chemostat (Bioflo, model C32), a source of bacterial growth media in a mixing chamber and several flow cells connected thereto. The flow cells were specifically designed to contain 13 mm×1 mm thick SCHAP disks prepared in accordance with the procedure of Example 1 on which plaque formation was measured.

A mixed culture of five species of oral microorganisms (*A. viscosus, S. mutans, S. sanguis, V. parvula*, and *F. nucleatum*) associated with human plaque was maintained in the Chemostat, and the culture was then pumped through the flow cells at the rate of 1 ml/minute for 48 hours to grow plaque on the disks. Thereafter, the liquid dentifrices were pumped for 30 seconds at the rate of 1 ml/minute through the flow cells containing SCHAP disks on which the plaque was grown. A total of four treatments of the SCHAP disks were given at 12 hour intervals during a 48 hour plaque growth period. Thereafter, bacterial plaque grown on the SCHAP disks was removed by immersion of the disks in a 2 ml solution of 0.1 N NaOH in a water bath at 37° C. with gentle shaking for 15 minutes. The disks were removed and the NaOH solution was sonicated to disperse the plaque. Turbidity (optical density, OD) of the sample was then determined by measuring the absorbance at 610 nm in a spectrophotometer which is turbidity reported as plaque score in Table III, below. Plaque scores indicate the degree of plaque growth on the SCHAP disks, that is the lower the plaque score, the greater the antiplaque efficacy of the dentifrice slurry being tested. The plaque scores of Compositions A, $C_1$, and $C_5$ are recorded in Table III, below.

TABLE III

| Composition | Plaque Score | Standard Deviation |
|---|---|---|
| A | 0.0317 | ±0.0094 |
| $C_1$ | 0.0485 | ±0.0046 |
| $C_5$ | 0.0411 | ±0.0067 |

The plaque scores recorded in Table III indicate Composition A containing a PAA-POE block copolymer of the present invention reduced plaque growth on SCHAP disks to a significantly greater degree, i.e., about 23% as compared to the control, Composition $C_5$ containing 2% by weight of Gantrez S-97, a maleic anhydride/vinyl ether copolymer known to enhance the antiplaque efficacy of Triclosan. Composition $C_1$ containing a PAA-POE block copolymer similar to that used in Composition A, but with a POE component having a weight average molecular weight of 20,000 which exhibited increased Triclosan uptake on SCHAP disks, was not as effective as Composition $C_5$ in reducing plaque growth on SCHAP disks. The results recorded in Table III demonstrate the criticality of the appropriate molecular weight of POE (between about 4,000 to about 20,000 g/mol) in the PAA-POE block polymer to provide not only increased antibacterial agent delivery but significantly enhanced Triclosan antiplaque efficacy as well.

EXAMPLE III

The procedure of Example I was repeated to prepare a dentifrice composition of the present invention except that 2% of a PAA-POE graft copolymer having a weight average molecular weight of 610,000 containing 20% by weight POE of weight average molecular weight of 20,000 ("Composition E") and 20% of a PAA-POE graft copolymer having a weight average molecular weight of 600,000 containing 2% by weight POE having a molecular weight of 20,000 ("Composition F") was substituted for the PAA-POE block copolymer used to prepare Composition A of Example I.

The uptake of Triclosan on SCHAP disks from Compositions E and F is recorded in Tables IV and V below. For purposes of control, 2% by weight of the maleic anhydride/vinyl ether copolymer, Gantrez S-97 was substituted for the PAA-POE graft copolymer to prepare a control dentifrice ("Composition $C_6$"). The Triclosan uptake from Composition $C_6$ is also recorded in Tables IV and V.

TABLE IV

| Composition | Triclosan Uptake (µg/disk) | Standard Deviation |
| --- | --- | --- |
| E | 111.43 | 2.13 |
| $C_6$ | 82.77 | 9.46 |

TABLE V

| Composition | Triclosan Uptake (µg/disk) | Standard Deviation |
| --- | --- | --- |
| F | 89.52 | ±7.64 |
| $C_6$ | 74.50 | ±4.36 |

The results recorded in Tables IV and V show that Compositions E and F containing 2% by weight of the PAA-POE graft copolymer delivered about 32% and 20% more Triclosan on SCHAP disks compared to compositions in which the maleic anhdyride/vinyl ether copolymer, Gantrez S-97, was used instead of the PAA-POE graft copolymer.

EXAMPLE IV

The procedure of Example II was repeated to evaluate the antiplaque efficacy of Composition E at two different polymer concentrations, namely 1.5% and 2.0% by weight. For comparative purposes, there was also evaluated Composition $C_6$ in which 2% by weight Gantrez S-97 was substituted for the PAA-POE graft copolymer of Composition E. A dentifrice composition which was similar to Composition E ("Composition $C_7$") except neither Triclosan or any copolymer was included in the dentifrice composition was used as a control. The results of these evaluations are recorded in Table VI below.

TABLE VI

| Composition | Wt. % Polymer | Plaque Score | Standard Deviation |
| --- | --- | --- | --- |
| E | 2.0 | 0.30 | ±0.09 |
| E | 1.5 | 0.33 | ±0.12 |
| $C_6$ | 2.0 | 0.37 | ±0.08 |
| $C_7$ | 0 | 0.57 | ±0.09 |

The results summarized in Table VI show that Composition E containing the PAA-POE graft copolymer reduced plaque growth on SCHAP disks to a greater degree than Composition $C_6$ (prepared using the maleic anhydride/vinyl ether polymer) and by about 47% at a 2.0% by weight copolymer concentration and 43% with 1.5% by weight PAA-POE graft copolymer concentration when compared to the control.

EXAMPLE V

In a further demonstration of the increased uptake of Triclosan on SCHAP disks effected by the presence in a dentifrice composition of a PAA-POE graft copolymer of the present invention, the procedure of Example I was repeated, except 2% by weight of a PAA-POE graft copolymer having a weight average molecular weight of 640,000 containing 20% by weight of a POE having a weight average molecular weight of 35,000 was substituted for the PAA-POE block copolymer used to prepare Composition A, the composition of Example V being designated "Composition G".

For purposes of comparison, the procedure of Example V was repeated except a comparative PAA-POE graft copolymer of a weight average molecular weight of 580,000 designated "Composition $C_8$", containing 20% by weight POE of weight average molecular weight of 100,000 was substituted at the 2% weight level, for the PAA-POE graft copolymer used to prepare Composition G. The Triclosan uptake results for Compositions G and $C_8$ are recorded in Table VII below.

TABLE VII

| Composition | Triclosan Uptake (µg/disk) |
| --- | --- |
| $C_7$ | 88.23 |
| $C_8$ | 72.35 |

What is claimed is:

1. An oral composition exhibiting increased antiplaque efficacy as compared to its antiplague activity as increased with maleic anhydride vinyl ether polymer comprising in an orally acceptable aqueous fluoride dentifrice or mouthwash dental product vehicle one which is retained in the oral cavity for a time sufficient to contact all of the dental surfaces but which is not intentionally ingested the vehicle containing an effective antiplaque amount of a noncationic antibacterial agent and an acrylic polymer/polyoxyalkylene block or graft copolymer having a weight average molecular weight of about 250,000 to about 1,000,000 the acrylic polymer component comprising about 75 to about 95% by weight of the copolymer and the polyoxyalkylene component comprising about 5 to about 25% by weight of the copolymer, the polyalkylene component of the block copolymer having a weight average molecular weight greater than about 4,000 and less than 20,000, and the polyalkylene component of the graft copolymer having a weight average molecular weight of about 10,000 to about 50,000.

2. The composition of claim 1 wherein the acrylic polymer is a polymer of an alpha, beta-ethylenically unsaturated carboxylic acid and the polyoxyalkylene is polyoxyethylene.

3. The composition of claim 2 wherein the alpha, beta-ethylenically unsaturated acid is acrylic acid.

4. The composition of claim 1 wherein the block or graft copolymer is a polyacrylic acid/polyoxyethylene copolymer having a weight average molecular weight of about 500,000 to about 1,000,000.

5. The composition according to claim 1 wherein the block or graft copolymer is present in the oral composition at a concentration of about 0.5 to about 5% by weight.

6. The composition of claim 1 wherein the noncationic antibacterial agent is incorporated in the composition at a concentration of about 0.05 to about 2.0% by weight.

7. The composition of claim 1 wherein the antibacterial agent is a halogenated diphenyl ether.

8. The composition of claim 1 wherein an anionic surfactant is incorporated in the composition at a concentration of about 0.5 to about 3% by weight.

9. The composition of claim 8 wherein the anionic surfactant is sodium lauryl sulfate.

10. A method for the treatment and prevention of bacterial plaque accumulation on teeth which comprises preparing an oral composition containing an orally acceptable aqueous fluoride dentifrice or mouthwash dental Product vehicle which composition is retained in the oral cavity for a time sufficient to contact all of the dental surfaces but which is not intentionally ingested the vehicle containing an effective therapeutic amount of a noncationic antibacterial agent and an acrylic polymer/polyoxyalkylene block or graft copolymer having a molecular weight of about 250,000 to about 1,000,000 and formed from about 75 to about 95% by weight of the acrylic polymer component and about 5 to about 25% by weight of the polyoxyalkylene component, the polyalkylene component of the block copolymer having a molecular weight greater than about 4,000 and less than 20,000 and the polyalkylene component of the graft copolymer having a molecular weight of 10,000 to 50,000 and then administering the composition to the oral cavity whereby the antibacterial compound exhibits increased antiplaque activity to dental tissue, as compared to its antiplague activity as increased with maleic anhydride vinyl ether polymer.

11. The method of claim 10 wherein the acrylic polymer is a polymer of an alpha, beta-ethylenically unsaturated carboxylic acid or a salt thereof and the polyoxyalkylene is polyoxyethylene.

12. The method of claim 11 wherein the alpha, beta-ethylenically unsaturated carboxylic acid is acrylic acid.

13. The method of claim 10 wherein the copolymer is a polyacrylic acid/polyoxyethylene copolymer having a weight average molecular weight of about 500,000 to about 1,000,000.

14. The method according to claim 10 wherein the block or graft copolymer is present in the oral composition at a concentration of about 0.5 to about 5% by weight.

15. The method of claim 10 wherein the antibacterial agent is incorporated in the composition at a concentration of a bout 0.05 to about 2.0% by weight.

16. The method of claim 10 wherein the antibacterial agent is a halogenated diphenyl ether.

17. The composition of claim 10 wherein an the anionic surfactant is incorporated in the composition at a concentration of about 0.5 to about 5.0% by weight.

18. The method of claim 17 wherein the anionic surfactant is sodium lauryl sulfate.

* * * * *